(12) United States Patent
Fink et al.

(10) Patent No.: US 11,684,256 B2
(45) Date of Patent: Jun. 27, 2023

(54) EYE MOVEMENT IN RESPONSE TO VISUAL STIMULI FOR ASSESSMENT OF OPHTHALMIC AND NEUROLOGICAL CONDITIONS

(71) Applicant: Ceeable, Inc., Somerville, MA (US)

(72) Inventors: Wolfgang Fink, Montrose, CA (US); John Cerwin, Gurnee, IL (US); Christopher P Adams, Somerville, MA (US)

(*) Notice: Subject to any disclaimer, the term of this patent is extended or adjusted under 35 U.S.C. 154(b) by 339 days.

(21) Appl. No.: 16/768,546

(22) PCT Filed: Dec. 1, 2018

(86) PCT No.: PCT/US2018/063522
§ 371 (c)(1),
(2) Date: May 29, 2020

(87) PCT Pub. No.: WO2019/109058
PCT Pub. Date: Jun. 6, 2019

(65) Prior Publication Data
US 2020/0305707 A1   Oct. 1, 2020

Related U.S. Application Data

(60) Provisional application No. 62/708,070, filed on Dec. 1, 2017.

(51) Int. Cl.
*A61B 3/113* (2006.01)
*A61B 5/16* (2006.01)
(Continued)

(52) U.S. Cl.
CPC ............ *A61B 3/113* (2013.01); *A61B 3/0025* (2013.01); *A61B 3/0041* (2013.01);
(Continued)

(58) Field of Classification Search
CPC ..... A61B 3/113; A61B 3/0025; A61B 3/0041; A61B 3/0091; A61B 3/024; A61B 3/085;
(Continued)

(56) References Cited

U.S. PATENT DOCUMENTS

| 10,712,576 B1 * | 7/2020 | McEldowney ....... G03H 1/0248 |
| 2008/0228242 A1 * | 9/2008 | Fink ........................ A61F 9/08 607/54 |

(Continued)

FOREIGN PATENT DOCUMENTS

| WO | 2017125422 A1 | 7/2017 | |
| WO | WO-2017125422 A1 * | 7/2017 | ............... A61B 3/08 |

OTHER PUBLICATIONS

International search report and written opinion for corresponding PCT/US18/63522 dated Feb. 21, 2019.

*Primary Examiner* — Mohammed A Hasan
(74) *Attorney, Agent, or Firm* — Elevated IP, LLC

(57) ABSTRACT

The present invention generally relates to apparatus, software and methods for assessing ocular, ophthalmic, neurological, physiological, psychological and/or behavioral conditions. As disclosed herein, the conditions are assessed using eye-tracking technology that beneficially eliminates the need for a subject to fixate and maintain focus during testing or to produce a secondary (non-optical) physical movement or audible response, i.e., feedback. The subject is only required to look at a series of individual visual stimuli, which is generally an involuntary reaction. The reduced need for cognitive and/or physical involvement of a subject allows the present modalities to achieve greater accuracy, due to reduced human error, and to be used with a wide variety of subjects, including small children, patients with physical disabilities or injuries, patients with diminished mental capacity, elderly patients, animals, etc.

20 Claims, 4 Drawing Sheets

(51) Int. Cl.
  *A61B 3/00* (2006.01)
  *A61B 3/024* (2006.01)
  *A61B 3/08* (2006.01)
  *A61B 3/117* (2006.01)
  *A61B 3/12* (2006.01)
  *A61B 5/00* (2006.01)
  *G06F 3/01* (2006.01)

(52) U.S. Cl.
  CPC ............ *A61B 3/0091* (2013.01); *A61B 3/024* (2013.01); *A61B 3/085* (2013.01); *A61B 3/1176* (2013.01); *A61B 3/12* (2013.01); *A61B 5/161* (2013.01); *A61B 5/162* (2013.01); *A61B 5/163* (2017.08); *A61B 5/165* (2013.01); *A61B 5/4064* (2013.01); *A61B 5/4094* (2013.01); *A61B 5/4818* (2013.01); *A61B 5/4845* (2013.01); *A61B 5/6803* (2013.01); *A61B 5/7267* (2013.01); *A61B 5/7282* (2013.01); *G06F 3/013* (2013.01)

(58) Field of Classification Search
  CPC ......... A61B 3/1176; A61B 3/12; A61B 5/161; A61B 5/162; A61B 5/163; A61B 5/165; A61B 5/4064; A61B 5/4094; A61B 5/4818; A61B 5/4845; A61B 5/6803; A61B 5/7267; A61B 5/7282; A61B 3/032; A61B 5/4088; G06F 3/013
  USPC ........................................................ 600/558
  See application file for complete search history.

(56) References Cited

U.S. PATENT DOCUMENTS

| | | | |
|---|---|---|---|
| 2013/0308099 A1* | 11/2013 | Stack | A61B 5/6803 351/209 |
| 2017/0290504 A1 | 10/2017 | Khaderi et al. | |
| 2018/0043130 A1* | 2/2018 | Moore-Ede | A61M 21/02 |

* cited by examiner

EYE MOVEMENT IN RESPONSE TO VISUAL STIMULI FOR ASSESSMENT OF OPHTHALMIC AND NEUROLOGICAL CONDITIONS

CROSS-REFERENCE TO RELATED APPLICATIONS

This application is a national stage application, filed under 35 U.S.C. § 371, of International Patent Application No. PCT/US18/63522, filed Dec. 1, 2018, which claims the benefit of and priority to U.S. Provisional Patent Application No. 62/708,070, filed Dec. 1, 2017, both of which are hereby incorporated by reference in their entireties.

STATEMENT REGARDING FEDERALLY SPONSORED RESEARCH

None.

BACKGROUND

Vision is the primary sense used by humans in daily life, but over 285 million people in the world are visually impaired, of whom 39 million are blind and 246 million have moderate to severe visual impairment. The leading cause of blindness is cataract, which is readily treatable through surgery. Glaucoma is the 2nd leading cause of blindness in the world. In contrast to cataract, glaucoma is not curable. At best, the progression of visual field loss due to glaucoma can be stopped or delayed. Age-related macular degeneration (AMD), the 3rd leading cause of blindness, is generally not curable, and vision loss due to diabetic retinopathy is a developing epidemic. Therefore, there is an urgent need for the development of early detection methods and the deployment of timely countermeasures.

In addition to ophthalmic conditions, many neurological conditions can be diagnosed, assessed, classified, graded and/or treated using visual tracking modalities. With increased attention to threats or adverse effects to brain health, such as concussions and traumatic brain injuries (TBI) resulting from, e.g., military activities, contact sports and athletic activities, as well as post traumatic stress disorder resulting from a wide variety of circumstances, new methods for reliably and objectively identifying injuries and facilitating recovery are needed.

However, existing visual opthalmic and neurological tests typically require a subject to fixate for an extended period of time without losing focus and to actively respond to qeues from the test protocol with physical movements or audible indications, i.e., feedback. These requirements limit the accuracy and thereby clinical useability of test results due to human error and prevent testing of subjects that are incapable of meeting the test criteria (e.g., small children, patients with physical disabilities or injuries, patients with diminished mental capacity, elderly patients, animals, etc.).

US Patent Pub. No. 2017/0290504 discloses the use of gaming applications where visual tracking of multiple objects is used to test users' vision performance and to create visual profiles for users of virtual, augmented or mixed reality systems. The vision profiles for user groups become available to developers for use in modifying media to better align with users' visual characteristics, but the gaming applications are not altered ad hoc to probe users' visual deficiencies. In particular, US Patent Pub. No. 2017/0290504, for example, does not disclose an opportunistic testing of users' vision performance based on their individual responses throughout the testing.

SUMMARY

The present invention generally relates to apparatus, software and methods for assessing (e.g., detecting, classifying, grading and/or treating) ocular, ophthalmic, neurological, physiological, psychological and/or behavioral conditions. As disclosed herein, the conditions are assessed using eye-tracking technology that beneficially eliminates the need for a subject to fixate and maintain focus during testing or to produce a secondary (non-optical) physical movement or audible response, i.e., feedback. The subject is only required to look at a series of individual visual stimuli, which is generally an involuntary reaction. The reduced need for cognitive and/or physical involvement of a subject allows the present modalities to achieve greater accuracy, due to reduced human error, and to be used with a wide variety of subjects, including small children, patients with physical disabilities or injuries, patients with diminished mental capacity, elderly patients, animals, etc. Further, the use of opportunistic algorithms in some embodiments of the present apparatus, software and methods allows for the dense collection of data at locations of a potential problem and sparser collection of data elsewhere, thereby potentially shortening testing time while more accurately capturing problem locations, such as, but not limited to, visual field defects or scotomas.

The apparatus, software and methods disclosed herein may also be used to improve ophthalmic and/or neurological performance. For example, the apparatus, software and methods may be used to gauge and improve (train) reaction time and accuracy to stimuli for an athlete, pilot, astronaut, first responder, military participant (e.g., warfighter), etc. They may also be used to gauge and improve (train) reaction time and accuracy to stimuli for persons with neurological (or other) injuries and/or diseases.

In an aspect, an apparatus for assessing at least one of an ocular, ophthalmic, neurological, physiological, psychological or behavioral condition comprises a light-emitting device configured for displaying a series of individual visual stimuli to a subject; at least one sensor for tracking eye movement of the subject in response to each of the individual visual stimuli and generating data indicative of the tracked eye movement; and a processor for (i) analyzing the data indicative of the tracked eye movement; (ii) instructing the light-emitting device to display the individual visual stimuli, wherein at least one stimulus in the series of individual visual stimuli is placed opportunistically; and (iii) assessing the presence, absence, type and/or extent of the ocular, ophthalmic, neurological, physiological, psychological and/or behavioral condition.

In an embodiment, an opportunistic placement is based on a subject's response to at least one prior stimulus, a subject's response to only one stimulus, a subject's response to only the immediately preceding stimulus, or a subject's response to a plurality of prior stimuli.

In an embodiment, the apparatus further comprises memory for storing data indicative of the tracked eye movement.

In an embodiment, a processor of the apparatus executes at least one of a deterministic algorithm, a non-deterministic algorithm, a stochastic algorithm, a machine learning algorithm, a deep learning algorithm or a combination thereof.

In an embodiment, the apparatus comprises a virtual reality headset, an augmented reality headset, a mixed reality headset or another device with a built-in or auxiliary eye-tracking device.

In an embodiment, a sensor for tracking eye movement of the subject is selected from the group consisting of a camera, an infrared sensor and combinations thereof.

In an embodiment, a light-emitting device displays visual stimuli monocularly or binocularly to test a subject. Regardless of whether the testing is monocular or binocular, eye/gaze tracking data may be collected monocularly (for the eye receiving the visual stimuli or for the eye that is not receiving the visual stimuli) or binocularly (even if only one eye is receiving the visual stimuli).

In an embodiment, an assessment of at least one of an ocular, ophthalmic, neurological, physiological, psychological or behavioral condition comprises presenting only one visual stimulus to a subject with a light-emitting device; tracking the subject's gaze in response to the visual stimulus with a sensor configured to acquire eye movement data; analyzing the data indicative of the tracked eye movement; and assessing the presence, absence, type and/or extent of the ocular, ophthalmic, neurological, physiological, psychological and/or behavioral condition.

In an embodiment, the light-emitting device may display the visual stimuli as a point of light on a background or an illuminated object or shape, wherein the light, the background, and/or the object or shape are black, white, colored, opaque, translucent, textured, of varied contrast, steady or flickering at a predetermined or opportunistically determined frequency, or combinations thereof. In an embodiment, the light-emitting device displays the visual stimuli on a parallel plane, a warped plane, an irregular plane, a convex surface, a concave surface, or in 3D space. For example, the light-emitting device may comprise a projector, a light-emitting diode, a light bulb, a fluorescing body, a liquid crystal, an electroluminescent particle, electronic ink, a cathode ray tube (CRT), a laser, a carbon nanotube, plasma, a quantum dot and combinations thereof. In an embodiment, the light-emitting device displays the visual stimuli on a physical surface/object or a generated or virtual surface/object. For example, the light-emitting device may display the visual stimuli on a display screen, a wall, a building, a point cloud, or a physical object.

In an embodiment, a subject is a human or a non-human animal. For example, a subject may be a patient, an athlete, a pilot, an astronaut, a driver, a military participant, a civilian, an equipment or machinery operator, or a first responder. In an embodiment, a subject may be a non-human mammal such as a canine, a feline, a porcine, a bovine, an equine, an ovine, a murine or the like.

In an embodiment, data indicative of eye movement are representative of the subject's central vision, the subject's peripheral vision, or both. In other words, apparatus, software and methods of the present invention are capable of performing campimetry, perimetry or both.

In an embodiment, data indicative of eye movement is spatial data, temporal data or spatiotemporal data. In an embodiment, data indicative of eye movement comprises gaze coordinates or gaze coordinates as a function of time. In an embodiment, gaze coordinates are selected from the group consisting of polar coordinates, Cartesian coordinates, pixel coordinates, spherical coordinates, cylindrical coordinates and combinations thereof.

In an embodiment, analyzing the stored data comprises extracting one or more observables, correlating one or more gaze coordinates with a field of view or combinations thereof. For example, the one or more observables may be selected from the group consisting of visual detection, gaze trajectory, response time, visual acuity, ability to fixate, overshoot/undershoot, saccadic movement, micro-saccadic movement, field of view, quality of the subject's central vision, quality of the subject's peripheral vision, eye coordination, strabismus, color vision, contrast sensitivity, object perception, shape perception, texture perception, flicker frequency perception and combinations thereof.

In an embodiment, an apparatus further comprises an output device for reporting at least one of the tracked eye movement(s) and the presence, absence, type and/or extent of at least one ocular, ophthalmic, neurological, physiological, psychological, or behavioral condition. In an embodiment, the output device is a graphical interface, a text interface, a VR (Virtual Reality)/AR (Augmented Reality)/MR (Mixed Reality) interface, a printer, a text and/or graphical report n physical or digital form, an audio or video signal output or a set of outputs.

In an embodiment, the ocular, ophthalmic, neurological, physiological, psychological, or behavioral condition is selected from the group consisting of retinal defects, optic nerve defects, cortical defects, blindness, color blindness, macular degeneration, concussion, traumatic brain injury (TBI), brain damage, diabetic retinopathy, glaucoma, cataract, epilepsy, post traumatic stress disorder (PTSD), strabismus, lazy eye tendencies, metamorphopsia, saccades, micro-saccades, influence of intoxicants, general eye coordination, alertness, sleep apnea and combinations thereof.

In an aspect, a non-transitory computer-readable medium for assessing at least one of an ocular, ophthalmic, neurological, physiological, psychological or behavioral condition comprises instructions stored on the computer-readable medium that when executed on a processor cause the processor to: instruct a light-emitting device to display a series of individual visual stimuli to a subject, wherein at least one stimulus in the series of individual visual stimuli is placed opportunistically; acquire data from at least one sensor that tracks eye movement of the subject in response to each of the individual visual stimuli; analyze the data indicative of the tracked eye movement; and assess the presence, absence, type and/or extent of the ocular, ophthalmic, neurological, physiological, psychological and/or behavioral condition.

In an embodiment, the non-transitory computer-readable medium further comprises instructions for storing data indicative of the tracked eye movement to memory. In an embodiment, the non-transitory computer-readable medium further comprises instructions for reporting an assessment of the ocular, ophthalmic, neurological, physiological, psychological and/or behavioral condition on an output device.

In an aspect, a method of assessing at least one of an ocular, ophthalmic, neurological, physiological, psychological, or behavioral condition of a subject using a computing device programmed to execute a plurality of programmatic instructions, comprises: presenting a series of individual visual stimuli to a subject with a light-emitting device coupled to the computing device, wherein at least one stimulus in the series of individual visual stimuli is placed opportunistically; tracking the subject's gaze in response to each of the individual visual stimuli with a sensor configured to acquire eye movement data; analyzing the data indicative of the tracked eye movement; and assessing the presence, absence, type and/or extent of the ocular, ophthalmic, neurological, physiological, psychological and/or behavioral condition.

In an embodiment, the step of presenting the series of visual stimuli comprises presenting a first stimulus in a first location and presenting a second stimulus in a second location different from the first location or the same as the first location, e.g. for repeat measurements.

BRIEF DESCRIPTION OF THE DRAWINGS

Illustrative embodiments of the present invention are described in detail below with reference to the attached drawings, wherein.

DETAILED DESCRIPTION

Figure 1:
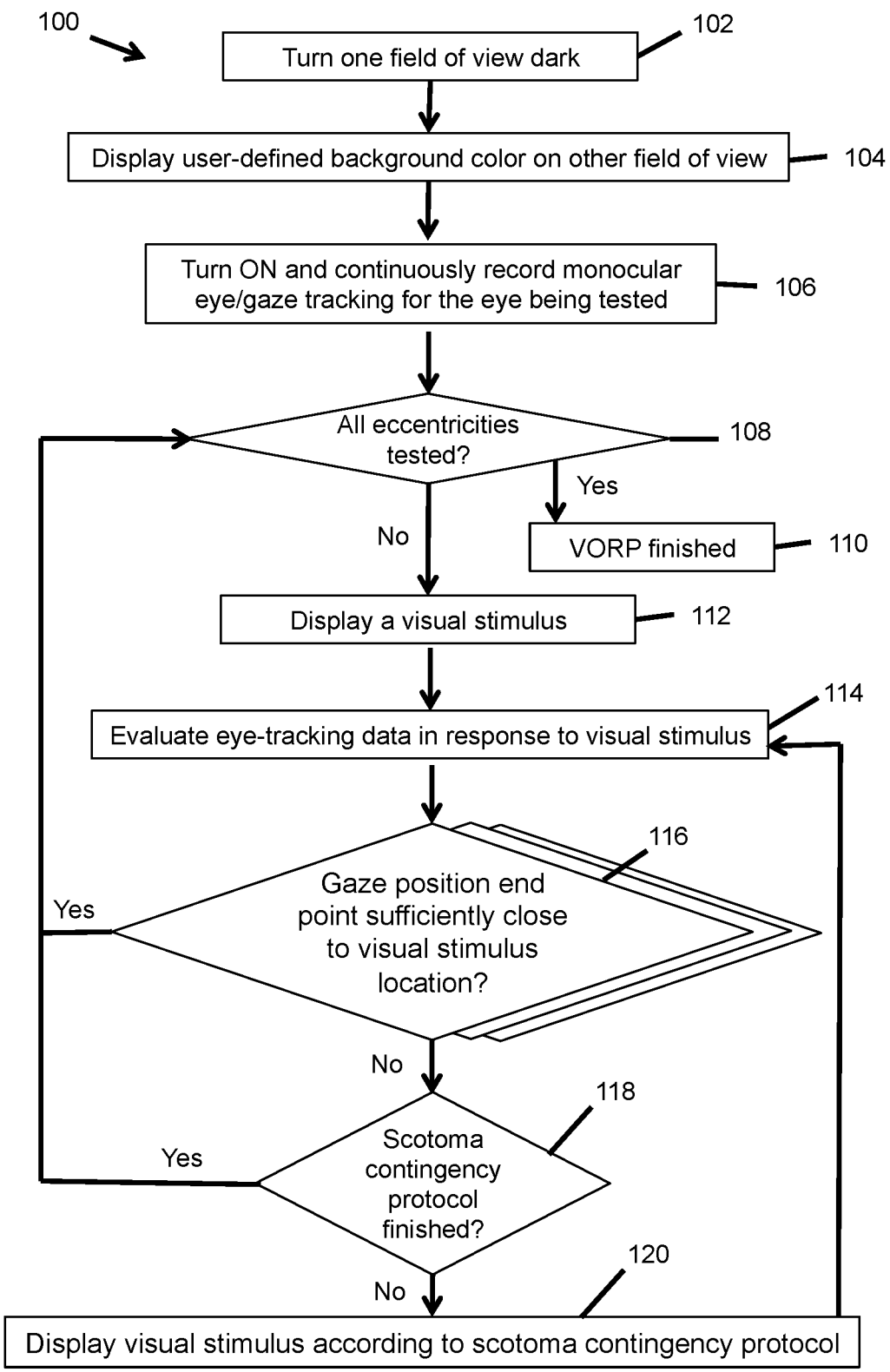
FIG. 1 is a flowchart illustrating exemplary steps within a virtual opportunistic reaction perimetry (VORP) test protocol.

In general, the terms and phrases used herein have their art-recognized meaning, which can be found by reference to standard texts, journal references and contexts known to those skilled in the art. The following definitions are provided to clarify their specific use in the context of this description.

As used herein, "virtual reality (VR)" refers to an immersive computer-simulated fully artificial digital environment, or the computer-generated simulation of a three-dimensional image or environment that can be interacted with in a seemingly real or physical way by a person using special electronic equipment, such as a helmet with a screen inside and/or gloves fitted with sensors.

As used herein, "augmented reality (AR)" refers to technology that superimposes a computer-generated image on a user's view of the real world, thus providing a composite view.

As used herein, "mixed reality (MR)" refers to a hybrid reality where virtual objects are overlaid upon and anchored to the real world such that the user can interact with the virtual objects.

As used herein, "opportunistic" describes something that is dependent upon an earlier result. Therefore, an "opportunistic visual stimulus" or "an opportunistically placed visual stimulus" is dependent upon a subject's response or non-response to at least one prior visual stimulus. For example, a subsequent visual stimulus that is opportunistically placed may be positioned to confirm a prior result or map the boundaries of an identified weakness or deficiency, e.g., a visual field defect or scotoma.

As used herein, a "series" includes two or more items, and a "series of individual visual stimuli" includes two or more visual stimuli that are individually displayed (i.e., the stimuli in the series are presented one at a time).

As used herein, the terms "eye movement" and "gaze movement" are used interchangeably to refer to a physiological response to a stimulus from a subject's eye(s). In addition, the terms "eye tracking" and "gaze tracking" are used interchangeably to refer to sensor output that is representative of the eye/gaze movement. In some embodiments, the sensor output is converted into "eye coordinates" or "gaze coordinates", which may be used interchangeably herein.

As used herein, "eccentricity" refers to the location of a light/visual stimulus with respect to a subject's current gaze location.

As used herein, a "deterministic algorithm" is an algorithm which, given a particular input, will always produce the same output, with the underlying machine always passing through the same sequence of states.

As used herein, a "non-deterministic algorithm" or "stochastic algorithm" or "probabilistic algorithm" is an algorithm which, given a particular input, will in general not produce the same output, with the underlying machine in general not passing through the same sequence of states. Such algorithm usually includes an element of randomness.

As used herein, a "machine learning algorithm" refers to an algorithm that builds or learns a mathematical model based on sample data in order to make predictions or decisions without being explicitly programmed to perform the task. Machine learning algorithms comprise, but are not limited to: logistic regression algorithms; decision trees; ensemble methods; level-set methods; cognitive maps; generalized linear models; and clustering algorithms.

As used herein, "deep learning" refers to a class of machine learning algorithms that use a cascade of multiple layers of nonlinear processing units for feature extraction and transformation. Each successive layer uses the output from the previous layer as input. For example, deep learning algorithms comprise, but are not limited to: feedforward networks, multi-layer perceptrons, convolutional networks, recurrent neural networks, extreme learning machines, long/short term memory networks, auto encoders, modular neural networks, Hopfield attractor networks.

"Proximal" and "distal" refer to the relative positions of two or more objects, planes or surfaces. For example, an object that is close in space to a reference point relative to the position of another object is considered proximal to the reference point, whereas an object that is further away in space from a reference point relative to the position of another object is considered distal to the reference point.

The terms "direct and indirect" describe the actions or physical positions of one object relative to another object. For example, an object that "directly" acts upon or touches another object does so without intervention from an intermediary. Contrarily, an object that "indirectly" acts upon or touches another object does so through an intermediary (e.g., a third component).

FIG. 1 is a flowchart 100 illustrating exemplary steps within a virtual opportunistic reaction perimetry (VORP) test protocol carried out, for example, on a VR, AR or MR head mounted display. In step 102, one field of view is turned dark. In other words, the input for one eye that is not being tested is set to a dark or black background to accomplish monocular testing of the other eye. This input remains inactive/static during testing of the other eye. In step 104, the other field of view for the tested eye is set to a user-defined color (usually black). In step 106, monocular eye/gaze tracking for the eye being tested is turned ON, and stays ON for the entire test and eye/gaze tracking data are recorded. In a separate instantiation (not shown), gaze tracking for both eyes may be turned ON and/or gaze tracking may be turned ON only when a visual stimulus is presented. Step 108 is a query to determine whether all eccentricities or visual stimulus locations have been tested. If the answer to query 108 is yes, the VORP test is finished, as indicated in step 110. If the answer to query 108 is no, a visual stimulus is displayed (step 112) and eye/gaze tracking data associated with the subject's response to the visual stimulus are evaluated (step 114). The location of a visual stimulus may be selected, for example, according to user-defined specifications and/or an outside control algorithm, such as a lookup table or map or an opportunistic algorithm. If a lookup table/map is used, a visual stimulus is placed in a location with respect to the current eye/gaze position that most closely matches the eccentricities of an untested location on the lookup table/map. If an opportunistic control algorithm is used, the visual stimulus is placed in a location with respect to the current eye/gaze position that not only delivers a previously untested eccentricity, but may also zoom in and map out or delineate an area where the subject may have exhibited atypical behavior, e.g., a visual field defect or scotoma. Note, that subsequent visual stimuli locations are dependent upon a subject's current eye/gaze position because the subject may not return his or her gaze to a neutral position after every stimulus event. This ability of the present apparatus, software and methods to adapt to current conditions in real time alleviates the burden on the subject to maintain focus and remember to return to the neutral position after each visual stimulus is presented, and it improves results by eliminating or reducing human error.

Step 116 is a query to determine whether the subject's gaze position end point was sufficiently close to the visual stimulus location. If the answer to query 116 is yes, the method returns to step 108 to determine whether all eccentricities/locations have been tested. If the answer to query 116 is no, meaning that the gaze position end point was not sufficiently close to the visual stimulus location or there was no subject response to the visual stimulus at all, a second query 118 determines whether a scotoma contingency protocol is finished. If the answer to query 118 is yes, the scotoma contingency protocol is finished even though the last gaze position end point was not sufficiently close to the visual stimulus location (e.g., which may occur when a visual defect or scotoma is identified and confirmed), and the test continues with step 108. If the answer to query 118 is no, meaning the scotoma contingency protocol is not finished, a visual stimulus is displayed according to the scotoma contingency protocol (step 120) and eye tracking data associated with the subject's response to the visual stimulus are evaluated (step 114). The scotoma contingency protocol may, for example, retest the exact same eccentricity that caused a negative response to query 116 to confirm the result, retest the same eccentricity that caused the negative response to query 116 with a different color, contrast, shape, brightness, texture, flicker frequency or other characteristic, singularly or in any combination, to determine the cause of the result, test one or more eccentricities near the eccentricity that caused a negative response to query 116 thereby mapping the boundaries of a potential defect (e.g., visual field defect or scotoma), or a combination of the above. The notion of the subject's gaze position end point being sufficiently close to a visual stimulus location can be based, e.g., on a distance measure, such as, but not limited to the Euclidean distance between the subject's gaze position end point and the visual stimulus location, or on an angle measure, such as the visual field angle between the subject's gaze position end point and the visual stimulus location. In some embodiments, sufficiently close end points are less than or equal to 3 degrees of visual field from the visual stimulus location, or less than or equal to 2 degrees of visual field from the visual stimulus location, or less than or equal to 1 degree of visual field from the visual stimulus location, or less than or equal to 0.5 degree of visual field from the visual stimulus location. In an embodiment, a sufficiently close end point may be defined by a Euclidean distance within any of the immediately preceding ranges.

Flowchart 100 illustrates exemplary steps, which may be modified for different test purposes. For example, step 116 may include additional or alternative queries, such as did the subject overshoot/undershoot the visual stimulus location? Was the response time under or over a particular threshold? Has the visual stimulus location been tested a predetermined number of times? Was the eye/gaze trajectory sufficiently linear?

Figure 2:
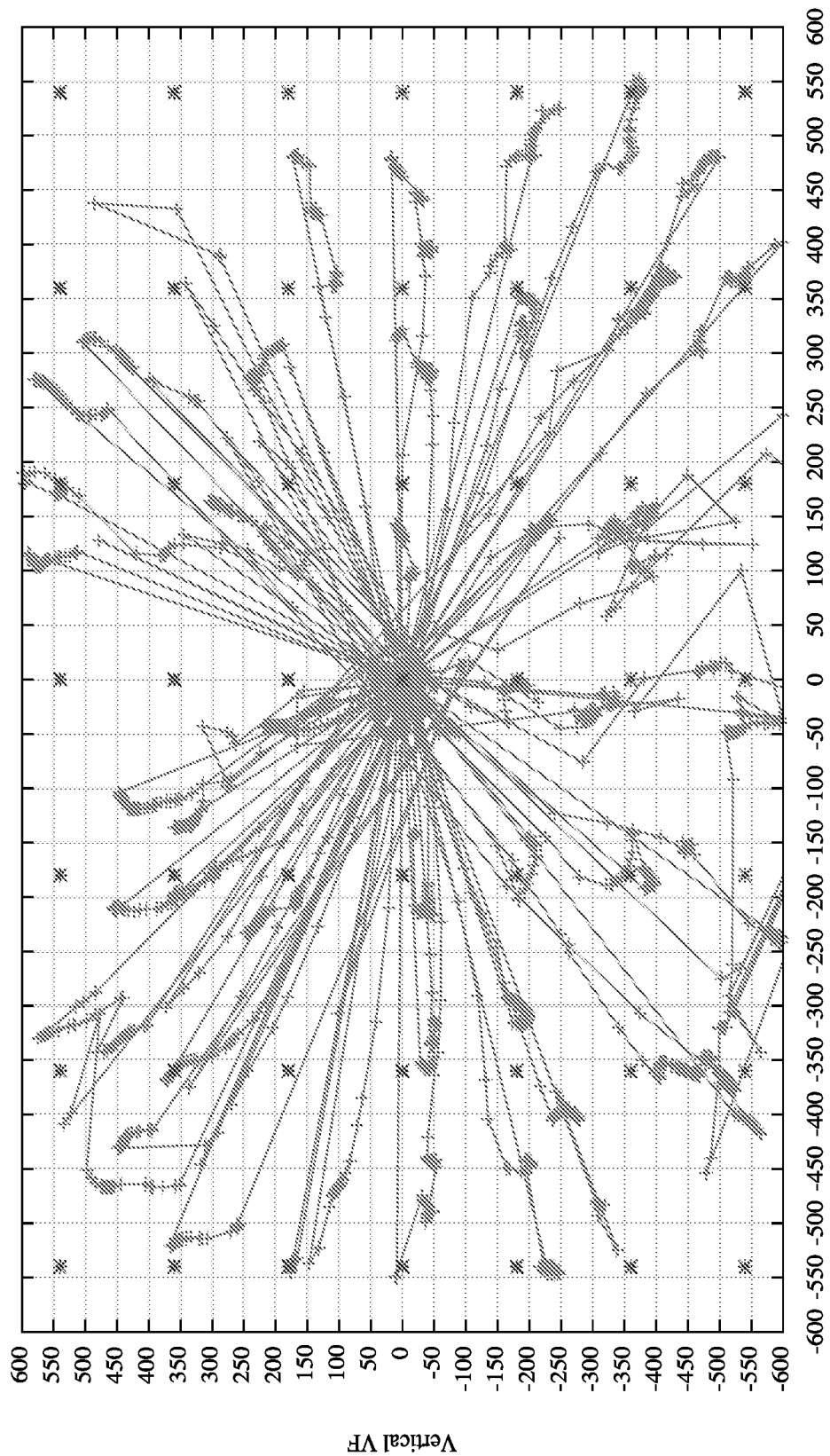
FIG. 2 is an example of a corrected examination log plot showing a compilation of VORP test data.

FIG. 2 is an example of a corrected examination log (i.e., log of the examination) plot showing a compilation of VORP test data. The plot area represents the visual field of a subject with the horizontal range on the x-axis and the vertical range on the y-axis. "X" marks indicate the positions of the visual stimuli presented to the subject over the course of the test. The visual stimuli were presented to the subject individually (i.e., one at a time) with the prior stimulus removed before a subsequent stimulus was presented. The lines show the subject's gaze trajectory toward each stimulus in response to that stimulus.

Figure 3:
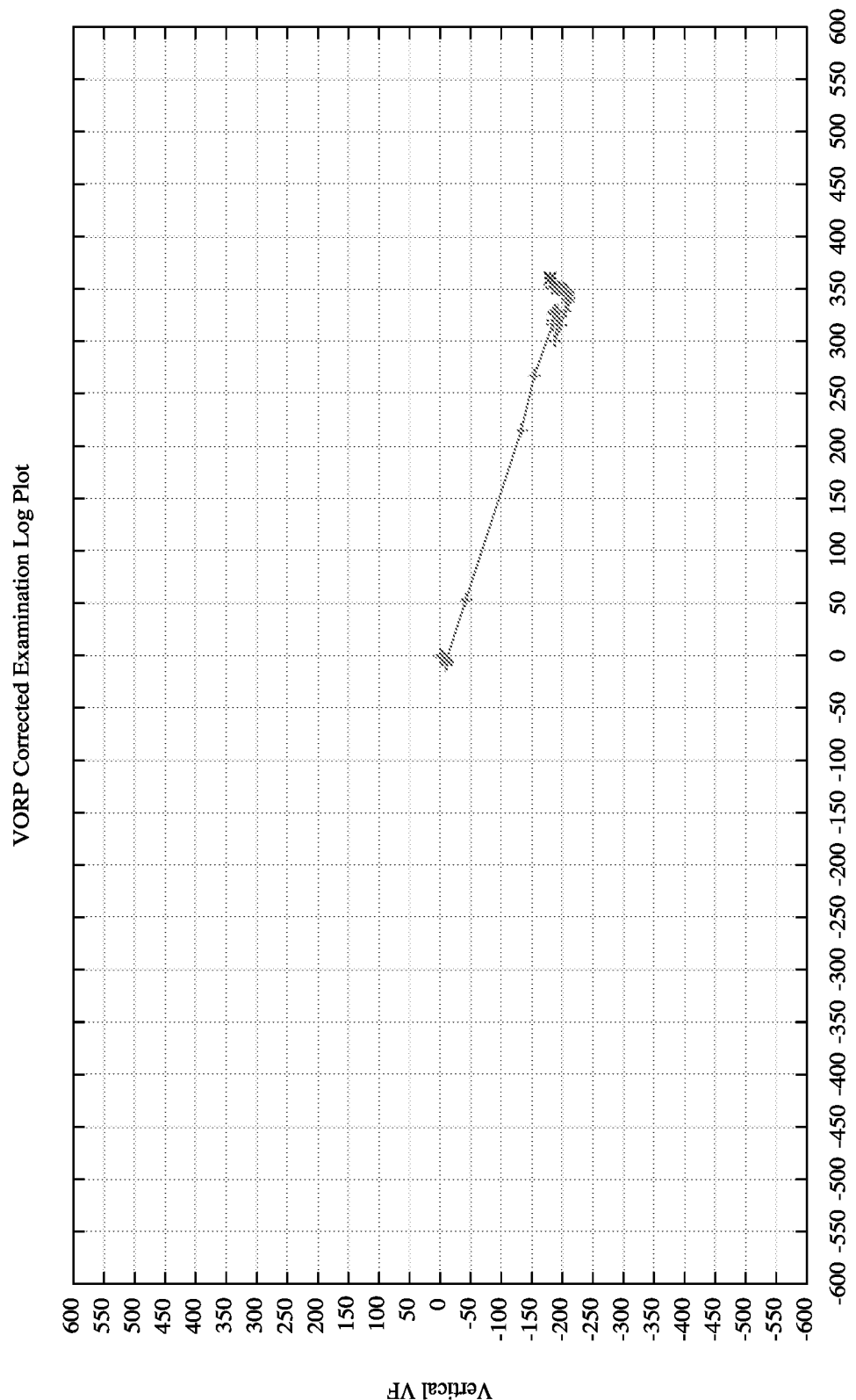
FIG. 3 is an example of an individual visual stimulus of FIG. 2 and corresponding gaze trajectory data in response to that visual stimulus.

FIG. 3 is an example of an individual visual stimulus of FIG. 2 and corresponding gaze trajectory data in response to that visual stimulus.

Figure 4:
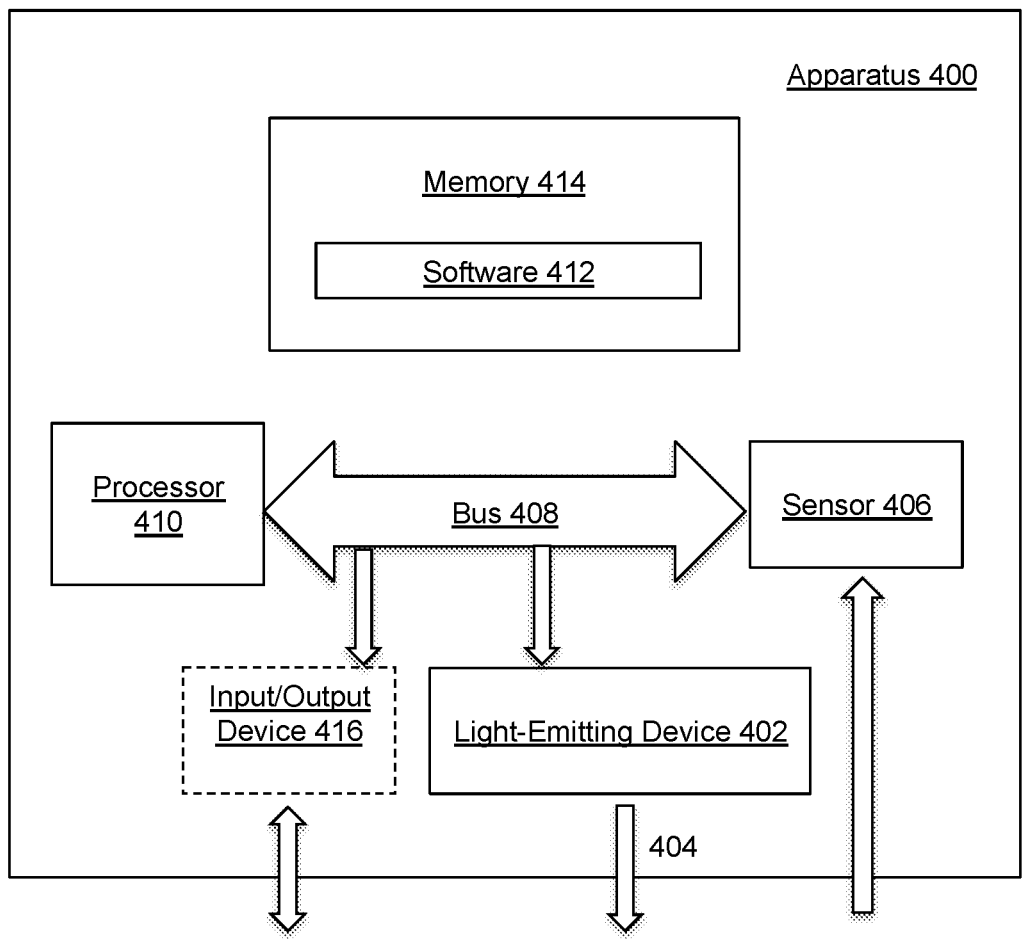
FIG. 4 is a block diagram of an exemplary apparatus for assessing at least one ocular, ophthalmic, neurological, physiological, psychological, or behavioral condition.

FIG. 4 is a block diagram of an exemplary apparatus 400 for assessing at least one ocular, ophthalmic, neurological, physiological, psychological, or behavioral condition. Apparatus 400 comprises a light-emitting device 402 configured for displaying a series of individual visual stimuli, represented by arrow 404, to a subject. At least one sensor 406 tracks eye/gaze movement of the subject in response to each of the individual visual stimuli and generates data indicative of the tracked eye/gaze movement. The data are sent to bus 408, and then to storage (not shown) or to a processor 410. Processor 410 instructs light-emitting device 402 to display/opportunistically place visual stimuli, analyzes data indicative of the tracked eye/gaze movement by executing software 412 stored in memory 414, and ultimately, assesses the presence, absence, type and/or extent of the ocular, ophthalmic, neurological, physiological, psychological and/or behavioral condition. In an embodiment, the information generated in the assessment step may be reported on an output device 416.

Although FIG. 4 illustrates one apparatus 400, structures and functionality presented as a single component may be implemented as separate components. For example, processor 410, memory 414 and software 412 may reside within an external computer that communicates with a VR/AR/MR headset through an input/output device 416. The VR/AR/MR headset may include light-emitting device 402 and sensor 406. Further, a single component, such as apparatus 400, may include multiple structures represented by a single block, e.g., multiple processors 410, light-emitting devices 402 and sensors 406, may be present in apparatus 400.

The one or more processors may also operate to support performance of the relevant functionality in a "cloud computing" environment or as a "software as a service" (SaaS). For example, at least some of the functions may be performed by a group of computers accessible via a network (e.g., the Internet) and via one or more appropriate interfaces (e.g., application program interfaces (APIs)).

The apparatus, software and methods disclosed herein are further illustrated by the following Example. This Example is for illustrative purposes only and is not intended to limit the invention.

EXAMPLE

This Example illustrates a virtual opportunistic reaction perimetry (VORP) test using a virtual reality head mounted display (VR HMD).

Equipment

A VR HMD (head mounted display) or equivalent with usually two video feeds, i.e., one for the left eye and one for the right eye, is used. The VR HMD is equipped with real-time eye tracking (preferably 60 Hz or more) for the left and right eye, respectively. For example, useful specifications are: infrared eye tracking system×2, tracking accuracy of less than 1 degree, frame rate of 120 fps.

DESCRIPTION

To test the central and peripheral vision of subjects, i.e., perimetry based on campimetry, point-like light stimuli are presented as a series of individual stimuli. As opposed to standard automated perimetry (e.g., using a Zeiss Humphrey Visual Field Analyzer), the subject is NOT required to maintain fixation throughout the entire test exam, nor is the subject required to push a button or provide verbal feedback to acknowledge the perception of a light stimulus.

Overview of VORP Procedure

The video feed for the eye not being tested is turned off or moved to a black or dark state. For the eye being tested, the eye tracking sensor constantly reports the current eye/gaze location. The subject is asked to "chase" perceived light stimuli that are being presented at pseudo-random locations within the field of view of the VR HMD and subject. In other words, given any current eye/gaze location, the governing test program (i.e., code) can calculate the location of a light stimulus for subsequent presentation within the available real estate of the VR HMD (i.e., the video feed for that eye) for an eccentricity/location that has not been covered at all or not sufficiently covered yet in the current test session. If the subject sees the stimulus and moves his eye/gaze to the location of that last stimulus, the governing test program can exploit this to opportunistically present a stimulus at a farther, same, or closer distance/eccentricity from the eye's current location. For example, if the subject focuses on the center of the VR HMD hemi-screen, and the horizontal dimension of the screen is 20 degrees to either side from center of fixation, a light stimulus presented at either 20 degree location would "force" the eye/gaze to go there. Once there, a light stimulus can be presented at the opposite end of the VR HMD hemi-screen, to now yield a 40 degree eccentricity location and visual field testing. That way, over time, a meaningful visual field can be tested. The overall time of the testing procedure is not fixed, and depends on how quickly the governing test program completes a sufficient visual field screening directly dependent on the eye/gaze movement, i.e., the response of the subject.

Detailed VORP Procedure (1) In an instantiation, generate a rectangular or concentric list/map of eccentricities to be tested. In the case of VORP, e.g., planar polar coordinates, i.e., radius and angle, are an ideal choice.

(2) This list/map can be user-defined or computer-generated or randomly generated or opportunistically generated in a dynamic fashion (i.e., in real time during the test).

(3) If the map/list is user-defined it can be interactively generated, uploaded via an external file, or communicated through another computer module, or any other means for computer system communication known in the art. Initially a simple configuration file can be used. Eventually, however, the map/list could be dynamically generated and communicated through another computer module that sits on board the VR HMD. For starters, this module would be a simple configuration file.

(4) A VR headset with binocular eye-tracking sensors is generally used because it allows for a determination of strabismus, eye-coordination, saccades and micro-saccades.

(5) Monocular testing is recommended, i.e., the eye not being tested should look at a black or dark screen during the entire time the other eye is being tested.

(6) The patient should ideally be dark adapted. Dark adaption could be accomplished, e.g., with the VR HMD or in a darkened room prior to testing.

(7) The patient is allowed to "look around" within the test space, i.e., he does not have to maintain any particular fixation.

(8) Further the patient is asked to "chase" any light stimuli he might see by trying to focus his eye/gaze on the stimuli. The light stimulus, in an instantiation, would be a point of light that appears in a fixed position. In other instantiations, it could be a constantly present point of light that is moving, but this would constitute a different psychophysical test modality (i.e., object tracking).

(9) Then the VORP testing procedure commences as follows: depending on where the patient eye focus is currently with respect to the boundaries of the tested area in the VR headset, one of the eccentricities (or closest approximation thereof) of the generated list/map that is (a) feasible with respect to the test area boundaries and (b) not yet tested for, is stimulated with a light stimulus of fixed, predefined or variable size, brightness, color, texture, and shape for a certain fixed, predefined or variable time. In addition, the stimulus may have a certain fixed, predefined or variable flicker frequency, or it could alternate between two or more colors and/or textures. VORP is an opportunistic testing procedure, meaning that wherever the current eye focus is NOT, is the preferred area to place the next light stimulus to see whether the patient can notice that light stimulus at that eccentricity with respect to where his current focus is. In addition, repeat testing of prior tested eccentricities and/or locations can occur with VORP in order to map out the boundaries and/or extents of defects, e.g., visual field defects or scotomas.

With smart and/or opportunistic placement of light stimuli, VORP is capable of checking most eccentricities on the predefined list/map, or, in addition or alternatively, to test predominantly in areas where the patient has missed previous light stimuli so as to map out the location, shape and extent of potential scotomas (i.e., visual field defects).

(10) The reaction of the patient's eye with respect to a light stimulus is monitored. Stimulus parameters that may be specified in VORP include, but are not limited to, stimulus size/diameter, stimulus brightness, stimulus color, stimulus contrast, stimulus duration, stimulus texture (Gabor filters), stimulus shape, stimulus flicker frequency, presentation speed of light stimuli, i.e., the time between two consecutive light stimuli, hold time of light stimulus, i.e., how long a light stimulus is presented (ON-time) or combinations thereof.

Stimulus size and brightness may help determine the threshold of contrast sensitivity of the retina at the particular location of the light stimulus. Stimulus color may help determine if the patient is more sensitive to certain colors than to others (e.g., green), and/or whether the patient suffers from a particular color blindness. Stimulus duration may help determine overall alertness of the patient (e.g., determining fatigue in sleep apnea patients, equipment or machinery operators, employees working extended shifts) and reaction speed of the patient (e.g., especially in the elderly). This may be used, e.g., by motor vehicle license issuers to determine the fitness of a subject for operating a vehicle (subsurface vehicle, surface vehicle, aerial vehicle or space vehicle) or machinery, or by safety regulators to determine when an employee is too fatigued to continue working. Stimulus texture may be used to determine particular deficiencies, e.g., deficiencies related to P-cells and/or M-cells. Stimulus shape may help identify metamorphopsia, e.g., distortions in the visual field.

The stimulus parameters/characteristics described herein could be supplied by an external configuration or initialization file to be loaded into a VORP apparatus, interactively chosen by the user/operator during VORP test setup, opportunistically chosen by the VORP program throughout the test, or communicated through another computer module, or any other means for computer system communication known in the art. For each exam the chosen stimulus characteristics/parameters used throughout the testing are documented and reported.

The background color may be changed, e.g., to enable a bright yellow background with large blue stimuli to emulate blue-yellow perimetry, also known as short wave automated perimetry (SWAP), for earlier Glaucoma detection.

At least the following observables may be recorded via eye/gaze tracking during the VORP testing procedure: tested eccentricity, direction/path/trajectory of gaze change, velocity of gaze change, overall reaction speed or alertness of a subject, achieved accuracy of focusing on the stimulus if at all, overshooting/undershooting the stimulus location, or meandering around the stimulus location. The direction, path, trajectory and velocity of gaze change may be indicative of brain damage, concussions, and traumatic brain injury (TBI).

(11) Points 9 and 10 continue until the entire generated list/map of eccentricities has been tested.

(12) Retesting of eccentricities can be performed to avoid/reduce false positives and false negatives, and/or for statistical purposes. Retesting of eccentricities can also be performed to further map out and/or delineate defects, e.g., visual field defects or scotomas.

(13) The choice of eccentricities from the generated list/map can be opportunistic, random within the confines of feasibility, or following a controlled protocol. An example of opportunistic eccentricity generation might include more targeted stimulus generation in areas of the visual field were an initial defect is detected early on in the test procedure. With smart/opportunistic placement of light stimuli, VORP is capable of checking most eccentricities on the predefined list/map, or, in addition or alternatively, of testing predominantly in areas where the subject has missed previous light stimuli so as to map out the location, shape and extent of potential scotomas (i.e., visual field defects).

(14) The possibility that a subject cannot see an eccentricity or eccentricities or all eccentricities (e.g., blind, color-blind, or too dim or small or fast of stimuli) is also taken into account and programmatically captured.

(15) Because this is opportunistic reaction perimetry, the overall testing time per eye may vary. For example, the VORP test time may depend on how quickly VORP completes a visual field screening given the subject's eye movement during the test in response to the presented visual stimuli. As such an overall maximum cutoff time for the test may be introduced.

Ocular, ophthalmic, neurological, physiological, psychological or behavioral conditions that may be tested for by VORP include but are not limited to: visual field testing (retinal testing, optic nerve testing, and cortical testing), TBI or other brain damage, concussions, early onset of AMD or diabetic retinopathy, early onset of glaucoma and cataract, epilepsy, strabismus, lazy-eye determination/assessment, metamorphopsia, general eye coordination, how quickly (i.e., speed) does the subject focus on any presented light stimulus (potential insight into TBI, PTSD, potential glaucoma, etc.), alertness, sleep apnea, how coordinated does the subject move his eye towards any presented light stimulus (potential insight into TBI, PTSD, potential glaucoma, etc.), ability to detect multiple defects in a single test (visual field defects and color blindness), visual field defects and reaction speed, saccades and micro-saccades, i.e., eye movement, ability to focus on or track light stimuli, which may be an indication of being under the influence of, e.g., legal or illegal drugs, intoxicants, biohazards (e.g., bacteria and viruses), biological substances, chemical substances, biochemical substances or radiation.

Statements Regarding Incorporation by Reference and Variations

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, and method steps set forth in the present description. As will be apparent to one of skill in the art, methods, software and apparatus/devices can include a large number of optional elements and steps. All art-known functional equivalents of materials and methods are intended to be included in this disclosure. Nothing herein is to be construed as an admission that the invention is not entitled to antedate such disclosure by virtue of prior invention.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a processor" includes a plurality of such processors and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is/are not specifically disclosed herein.

What is claimed is:

1. A non-transitory computer-readable medium for assessing at least one of an ocular, ophthalmic, neurological, physiological, psychological or behavioral condition comprising instructions stored on the computer-readable medium that when executed on a processor cause the processor to:
   instruct a light-emitting device to display a series of individual visual stimuli to a subject, wherein at least one stimulus in the series of individual visual stimuli is placed opportunistically;
   acquire data from at least one sensor that tracks eye movement of the subject in response to each of the individual visual stimuli;
   analyze the data indicative of the tracked eye movement; and
   assess the presence, absence, type and/or extent of the ocular, ophthalmic, neurological, physiological, psychological and/or behavioral condition.

2. The non-transitory computer-readable medium of claim 1, wherein the opportunistic placement is based on the subject's response to at least one prior stimulus, the subject's response to only one stimulus, the subject's response to only the immediately preceding stimulus, or the subject's response to a plurality of prior stimuli.

3. The non-transitory computer-readable medium of claim 1, wherein the instructions cause the processor to execute at least one of a deterministic algorithm, a non-deterministic algorithm, a stochastic algorithm, a machine learning algorithm, a deep learning algorithm or a combination thereof.

4. The non-transitory computer-readable medium of claim 1, wherein the light-emitting device displays the visual stimuli on a parallel plane, a warped plane, an irregular plane, a convex surface, a concave surface, or in 3D space.

5. The non-transitory computer-readable medium of claim 1, wherein the light-emitting device displays the visual stimuli on a physical surface or a generated surface.

6. The non-transitory computer-readable medium of claim 1, wherein the data indicative of eye movement comprises gaze coordinates or gaze coordinates as a function of time.

7. The non-transitory computer-readable medium of claim 1, wherein analyzing the data indicative of eye movement comprises extracting one or more observables selected from the group consisting of visual detection, gaze trajectory, response time, visual acuity, ability to fixate, overshoot/undershoot, saccadic movement, micro-saccadic movement, field of view, quality of the subject's central vision, quality of the subject's peripheral vision, eye coordination, strabismus, color vision, contrast sensitivity, object perception, shape perception, texture perception, flicker frequency perception and combinations thereof.

8. The non-transitory computer-readable medium of claim 1, wherein the condition is selected from the group consisting of retinal defects, optic nerve defects, cortical defects, blindness, color blindness, macular degeneration, concussion, traumatic brain injury (TBI), brain damage, diabetic retinopathy, glaucoma, cataract, epilepsy, post traumatic stress disorder (PTSD), strabismus, lazy eye tendencies, metamorphopsia, saccades, micro-saccades, influence of intoxicants, legal/illegal drugs, biohazards, biological substances, chemical substances, biochemical substances or radiation, general eye coordination, alertness, sleep apnea and combinations thereof.

9. A method of assessing at least one of an ocular, ophthalmic, neurological, physiological, psychological or behavioral condition of a subject using a computing device programmed to execute a plurality of programmatic instructions, comprising:
   presenting a series of individual visual stimuli to a subject with a light-emitting device coupled to the computing device, wherein at least one stimulus in the series of individual visual stimuli is placed opportunistically;
   tracking the subject's gaze in response to each of the individual visual stimuli with a sensor configured to acquire eye movement data;
   analyzing the data indicative of the tracked eye movement; and
   assessing the presence, absence, type and/or extent of the ocular, ophthalmic, neurological, physiological, psychological and/or behavioral condition.

10. The method of claim 9, wherein the opportunistic placement is based on the subject's response to at least one prior stimulus, the subject's response to only one stimulus, the subject's response to only the immediately preceding stimulus, or the subject's response to a plurality of prior stimuli.

11. The method of claim 9, wherein presenting the series of individual visual stimuli comprises presenting a first stimulus in a first location and presenting a second stimulus in a second location different from the first location or the same as the first location.

12. The method of claim 9, wherein the processor executes at least one of a deterministic algorithm, a non-deterministic algorithm, a stochastic algorithm, a machine learning algorithm, a deep learning algorithm or a combination thereof.

13. The method of claim 9, wherein the light-emitting device displays the visual stimuli on a parallel plane, a warped plane, an irregular plane, a convex surface, a concave surface, or in 3D space.

14. The method of claim 9, wherein the light-emitting device displays the visual stimuli on a physical surface or a generated surface.

15. The method of claim 9, wherein the data indicative of eye movement comprises gaze coordinates or gaze coordinates as a function of time.

16. The method of claim 9, wherein analyzing the data indicative of eye movement comprises extracting one or more observables selected from the group consisting of visual detection, gaze trajectory, response time, visual acuity, ability to fixate, overshoot/undershoot, saccadic movement, micro-saccadic movement, field of view, quality of the subject's central vision, quality of the subject's peripheral vision, eye coordination, strabismus, color vision, contrast sensitivity, object perception, shape perception, texture perception, flicker frequency perception and combinations thereof.

17. The method of claim 9, wherein the condition is selected from the group consisting of retinal defects, optic nerve defects, cortical defects, blindness, color blindness, macular degeneration, concussion, traumatic brain injury (TBI), brain damage, diabetic retinopathy, glaucoma, cataract, epilepsy, post traumatic stress disorder (PTSD), strabismus, lazy eye tendencies, metamorphopsia, saccades, micro-saccades, influence of intoxicants, legal/illegal drugs, biohazards, biological substances, chemical substances, biochemical substances or radiation, general eye coordination, alertness, sleep apnea and combinations thereof.

18. An apparatus for assessing at least one of an ocular, ophthalmic, neurological, physiological, psychological or behavioral condition comprising:
   a light-emitting device configured for displaying a series of individual visual stimuli to a subject;
   at least one sensor for tracking eye movement of the subject in response to each of the individual visual stimuli and generating data indicative of the tracked eye movement; and
   a processor for (i) analyzing the data indicative of the tracked eye movement; (ii) instructing the light-emitting device to display the individual visual stimuli, wherein at least one stimulus in the series of individual visual stimuli is placed opportunistically; and (iii) assessing the presence, absence, type and/or extent of the ocular, ophthalmic, neurological, physiological, psychological and/or behavioral condition.

19. The apparatus of claim 18, wherein the opportunistic placement is based on the subject's response to at least one prior stimulus, the subject's response to only one stimulus, the subject's response to only the immediately preceding stimulus, or the subject's response to a plurality of prior stimuli.

20. The apparatus of claim 18, wherein the apparatus comprises a virtual reality headset, an augmented reality headset or a mixed reality headset.

* * * * *